United States Patent [19]

Borchert et al.

[11] Patent Number: 5,648,551
[45] Date of Patent: Jul. 15, 1997

[54] PROCESS FOR THE PREPARATION OF HALOBENZALDEHYDES

[75] Inventors: Holger Borchert, Frankfurt; Thomas Gerdau, Eppstein; Jens Weiguny, Weiterstadt, all of Germany

[73] Assignee: Hoechst Aktiengesellschaft, Germany

[21] Appl. No.: 592,069

[22] Filed: Jan. 26, 1996

[30] Foreign Application Priority Data

Jan. 30, 1995 [DE] Germany ............. 195 02 805.8

[51] Int. Cl.⁶ ............................................. C07C 45/36
[52] U.S. Cl. ................................... 568/431; 568/437
[58] Field of Search .............................. 568/431, 437

[56] References Cited

U.S. PATENT DOCUMENTS

| 4,390,728 | 6/1983 | Daniel . |
| 4,885,412 | 12/1989 | Pennington et al. . |
| 5,136,104 | 8/1992 | Saito et al. . |

FOREIGN PATENT DOCUMENTS

| 0226640 | 7/1987 | European Pat. Off. . |
| 226640 | 7/1987 | European Pat. Off. . |
| 0430001 | 12/1993 | European Pat. Off. . |
| 0599214 | 6/1994 | European Pat. Off. . |
| 0298234 | 2/1992 | German Dem. Rep. . |
| 1202774 | 12/1963 | Germany . |
| 1202774 | 5/1966 | Germany . |
| 1295538 | 1/1970 | Germany . |
| 5 4109-938 | 8/1979 | Japan . |
| 5 4100-336 | 8/1979 | Japan . |
| 7607598 | 1/1978 | Netherlands . |
| 0495301 | 12/1975 | U.S.S.R. . |

OTHER PUBLICATIONS

Chemical Abstracts, vol. 080. No. 21; May 27, 1974; Columbus, Ohio, US; abstract No. 119931; Chopra B et al; "Oxidation of chlorotoluenes on bismuth oxide–molybdenum oxide"; p. 360.

*Primary Examiner*—Gary Geist
*Assistant Examiner*—Jean F. Vollano
*Attorney, Agent, or Firm*—Connolly and Hutz

[57] ABSTRACT

The invention relates to a process for the preparation of halobenzaldehydes of the formula (I):

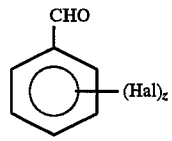

(I)

in which Hal is fluorine, chlorine, bromine or iodine and z=1, 2, 3 or 4, by catalytic gas-phase oxidation of a substituted toluene of the formula (II),

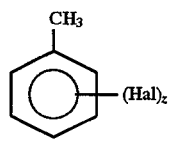
(II)

by oxygen, which comprises carrying out the oxidation in the presence of a catalyst of the formula (III)

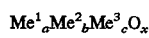

$$Me^1_a Me^2_b Me^3_c O_x \qquad (III),$$

in which $Me^1$ is bismuth or vanadium, $Me^2$ is at least one of the elements selected from the group consisting of lithium, sodium, potassium, rubidium and cesium, $Me^3$ is at least one element selected from the group consisting of iron, cobalt, nickel, niobium, molybdenum, arsenic, tin, antimony, tungsten, tantalum, phosphorus, chromium, manganese, palladium, copper, zinc, cerium, silver, boron, samarium, barium, calcium, magnesium and rhenium, and the letters a, b and c represent an atomic ratio of the respective elements such that when a=1, b has a value in the range from 0.1 to 2 and c has a value in the range from 0.05 to 2, different values for b and c being possible for different elements $Me^2$ or $Me^3$.

21 Claims, No Drawings

PROCESS FOR THE PREPARATION OF HALOBENZALDEHYDES

The invention relates to a process for the preparation of halobenzaldehydes by catalytic gas-phase oxidation of a substituted toluene with oxygen.

For the preparation of halobenzaldehydes, side-chain chlorination of toluenes with subsequent hydrolysis of the benzyl chlorides formed is known (DE 4 239 736). This process is not economically advantageous owing to high chlorine costs and complex waste water disposal. Other techniques described for the preparation of benzaldehydes which bear an electron-withdrawing substituent in one of the ortho- or parapositions are the liquid-phase oxidation of substituted β-aminostyrenes in the presence of copper salts (EP 0 430 001) and the liquid-phase oxidation of halotoluenes in the presence of cobalt salts and manganese salts (JP 54 100 336, JP 54 109 938). The disadvantages of these processes, apart from their extraordinary complexity, are the necessity for work-up of the solvents and regeneration of the metal salts.

For the preparation of benzaldehyde by gas-phase oxidation of the toluene with molecular oxygen, catalysts which are known are silver vanadate either alone or in combination with lead oxide and iron oxide (SU 495 301, DE 1 295 538, NL 7 607 598) and a mixed oxide catalyst comprising copper oxide, iron oxide, uranium oxide, lead oxide, tellurium oxide, molybdenum oxide and phosphorus oxide (U.S. Pat. No. 4,390,728). With this catalyst, at a conversion rate of 38%, benzaldehyde is formed with 64% selectivity.

Higher yields are obtained in the oxidation of methoxy-, phenoxy- or tert-butyl-substituted toluenes, which has been traced back to the positive inductive effect of these groups (Grybowska, 1987; Ueshima, 1992; Constantini, 1986). Thus, p-methoxytoluene and p-phenoxytoluene toluene can be oxidized to the corresponding aldehydes (EP 226 640) at 450° C. on a vanadium-thallium-cesium-antimony catalyst or a vanadium-cesium-potassium-phosphorus-iron-cobalt-oxide catalyst at a yield of over 75%. On the latter catalyst, in accordance with the weaker electron-donating effect of the tert-butyl substituent in comparison with the methoxy and phenoxy substituents, p-tert-butylbenzaldehyde is obtained with a yield of 56% (EP 226 640).

In contrast to toluenes having electron-donating substituents on the aromatic ring, hitherto only low yields have been obtained in the case of the gas-phase oxidation of halotoluenes which appears to confirm the preconception that high selectivities are not achievable in the case of electron-withdrawing substituents. According to DT 1 202 774, 2,6-dichlorotoluene can only be oxidized with a yield of 13% to the correspondingly substituted benzaldehyde on bismuth molybdate. The conversion rate with a single pass through the reactor is only 20%, although the reaction temperature is 580° C. In the case of oxidation of p-chlorotoluene in a sodium nitrate/potassium nitrate melt, the yield is actually only 4% (U.S. Pat. No. 4 885 412). The yields of 85% reported (DD 298 234) for the oxidation of p-chlorotoluene on oxovanadium(IV) diphosphate as catalyst cannot be achieved, as replicate experiments have shown. This catalyst can only achieve yields of 7% (see comparison Example 2).

There is therefore a requirement for a process which avoids the disadvantages mentioned and enables halobenzaldehydes to be obtained in high selectivity by the inexpensive direct oxidation of the substituted toluenes by molecular oxygen.

This object is achieved by a process for the preparation of halobenzaldehydes of the formula (I):

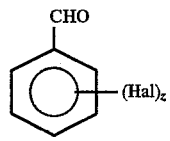

in which Hal is fluorine, chlorine, bromine or iodine and z=1, 2, 3 or 4, by catalytic gas-phase oxidation of a substituted toluene of the formula (II),

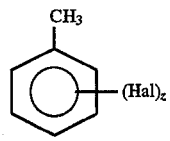

by oxygen, which comprises carrying out the oxidation in the presence of a catalyst of the formula (III)

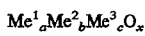

$$Me^1{}_aMe^2{}_bMe^3{}_cO_x \quad (III),$$

in which $Me^1$ is bismuth or vanadium, $Me^2$ is at least one of the elements selected from the group consisting of lithium, sodium, potassium, rubidium and cesium, $Me^3$ is at least one element selected from the group consisting of iron, cobalt, nickel, niobium, molybdenum, arsenic, tin, antimony, tungsten, tantalum, phosphorus, chromium, manganese, palladium, copper, zinc, cerium, silver, boron, samarium, barium, calcium, magnesium and rhenium, and the letters a, b and c represent an atomic ratio of the respective elements such that when a=1, b has a value in the range from 0.1 to 2 and c has a value in the range from 0.05 to 2, different values for b and c being possible for different elements $Me^2$ or $Me^3$.

Good results are achieved, for example, with a catalyst in which $Me^3$ is at least one element selected from the group consisting of iron, cobalt, nickel, niobium, molybdenum, arsenic, tin, antimony and rhenium.

When $Me^1$=vanadium, a combination A, in which $Me^2$ is cesium and $Me^3$ is at least one element selected from the group consisting of iron, niobium, arsenic, tin, antimony, rhenium and tungsten, in particular the combination $V_1Cs_{0.5-1}Fe_{0.5-2}(Nb, Sb, Sn, Re \text{ or } W)_{0.05-0.20}O_x$, proves to be particularly expedient. When $Me^1$=bismuth, a combination B, in which $Me^2$ is cesium and $Me^3$ is at least one element selected from the group consisting of molybdenum, tin, antimony, iron and cobalt, in particular the combination $Bi_1Cs_{0.5-2}(Sb \text{ and/or } Sn)_{0.2-1.5}O_x$ proves to be particularly expedient.

The catalyst can be present in pure form, mixed with a support material or fixed on a molded support material. Examples of support materials are alumina, ceramic, kieselguhr, silica gel, silicon carbide, fused silica, titanium dioxide and the like. Preferably, a catalyst of the composition A is fixed on a support material. A particularly preferred support material is titanium dioxide. A catalyst of the composition B is preferably used in pure form.

The starting materials of the individual components for the preparation of the novel catalyst are, in addition to the oxides, preferably water-soluble substances such as ammonium salts, nitrates, sulfates, halides, hydroxides and salts of organic acids which can be converted into the corresponding oxides by heating. To mix the components, aqueous solutions of the metal salts are prepared and mixed. The inert support can be suspended in this mixture. After evaporation, the catalyst precursor is molded at temperatures between 100° and 250° C., then calcined at 300° to 1000° C., preferably at 400° to 800° C. Calcination times which can be employed are 2 to 24 hours.

The reaction can be carried out in a fluidized bed or in a fixed-bed reactor. For use in a fluidized bed, the catalyst is ground to a particle size in the range from 10 μm to 200 μm. The oxidizing agent used is oxygen or an oxygen-containing gas such as air or a mixture of oxygen with an inert gas such as nitrogen, steam or noble gases. The use of air is preferred. The content of the halotoluene in the starting mixture can vary within a broad range, in which case, obviously, the self-ignition temperature and the explosion limits of the halotoluene need to be taken into account. The process is advantageously carried out by introducing the starting material stream comprising 0.5 to 5.0% by volume of halotoluene and 99.5 to 95.0% by volume of air into the reactor at a space velocity of 100 to 1000 h$^{-1}$ (STP=standard temperature and pressure: 273° K., 10$^5$Pa) at a reaction temperature of 400° to 500° C.

The process is of great industrial interest if 2-chlorotoluene, 4-chlorotoluene, 4-fluorotoluene or 2-bromotoluene is used.

The process is important for the preparation of compounds of the formula (I) in which Hal is fluorine, chlorine or bromine, in particular chlorine or bromine, preferably chlorine, and z=1 or 2, in particular 1.

EXAMPLES

Example 1

A solution of 10.0 g of ammonium metavanadate and 14.0 g of oxalic acid is prepared in warm water. To this solution are added 34.5 g of iron nitrate and 8.3 g of cesium nitrate. The mixture is stirred for one hour, then 6.0 g of titanium dioxide are added and the mixture is stirred for a further 30 minutes. The suspension is evaporated with stirring. After drying, the catalyst precursor is calcined at 500° C. for 6 hours. After cooling to room temperature, the catalyst is homogenized in a mortar and the powder is processed to a screening fraction (18 to 25 mesh).

To carry out the oxidation, 20 g of the catalyst is mixed with 20 g of broken quartz glass of the same screening fraction and this mixture is placed in a quartz glass tube having an inner diameter of 1.5 cm. For thermostating, the reactor is immersed in a fluidized sand bath which is heated externally. The starting material gas comprising 1% by volume of 4-chlorotoluene and 99% by volume of air is passed through the heated reactor at a total volumetric flow rate of 2.5 ml/s (STP) and the product is collected in a trap cooled to −70° C. Carbon monoxide and carbon dioxide are quantitatively determined by gas chromatography. The unreacted 4-chlorotoluene collected in the cold trap and the 4-chlorobenzaldehyde formed are taken up in acetonitrile and analyzed by HPLC. The results of the reaction are given in Table 1.

Example 2

The process described in Example 1 is carried out with the difference that 2.9 g of niobiumoxalate were additionally added to the aqueous solution. The results are given in Table 1.

Example 3

The process described in Example 1 is carried out with the difference that 2.0 g of tin chloride were additionally added to the aqueous solution. The results are given in Table 1.

Example 4

A solution of 10.0 g of ammonium metavanadate and 14.0 g of oxalic acid is prepared in warm water. To this solution are added 8.3 g of cesium nitrate and 4.9 g of potassium perrhenate. The mixture is stirred for one hour, then 7.9 g of titanium dioxide are added and the mixture is stirred for a further 30 minutes. The suspension is evaporated with stirring. After drying, the catalyst precursor is calcined at 500° C. for 6 hours.

The oxidation is carried out as described in Example 1 with the difference that the initial weight of catalyst was 40 g. The results are given in Table 1.

Example 5

The process described in Example 1 is carried out with the difference that 2.4 g of ammonium tungstate were additionally added to the aqueous solution.

The oxidation is carried out as described in Example 1 with the difference that the initial amount of catalyst was 10 g. The results are given in Table 1.

Example 6

A solution of 43.1 g of bismuth nitrate in 100 ml of 50% strength nitric acid is added dropwise to a solution of 26.5 g of ammonium heptamolybdate in 100 ml of water, where a pH of between 7 and 8 was established by addition of ammonia solution. 14.6 g of cesium nitrate, 4.0 g of iron nitrate, 2.9 g of cobalt nitrate, 14.6 g of antimony oxide and 15.1 g of tin oxide are then added and the mixture is slowly evaporated. After drying, the catalyst precursor is calcined at 600° C. for 12 hours. After cooling to room temperature, the catalyst is homogenized in a mortar and the powder is processed to a screening fraction (18 to 25 mesh).

The oxidation is carried out as described in Example 1 with the difference that the initial weight of catalyst was 10 g. The results are given in Table 1.

Example 7

The process described in Example 5 is carried out with the difference that 24.4 g of cesium nitrate, 4.0 g of iron nitrate, 2.9 g of cobalt nitrate, 59.3 g of antimony chloride and 45.1 g of tin chloride are added to the aqueous bismuth nitrate/ammonium molybdate mixture.

The oxidation is carried out as described in Example 1. The results are given in Table 1.

Example 8

The process described in Example 2 is carried out with the difference that, instead of 4-chlorotoluene, 2-chlorotoluene was used as the halotoluene. The results are given in Table 1.

Example 9

Example 6 is carried out with the difference that, instead of 4-chlorotoluene, 2-chlorotoluene is used as the halotoluene. The results are given in Table 1.

Example 10

The process described in Example 2 is carried out with the difference that, instead of 4-chlorotoluene, 4-fluorotoluene was used as the halotoluene. The results are given in Table 1.

Comparison Example 1

A solution of 43.1 g of bismuth nitrate in 100 ml of 50% strength nitric acid is added dropwise to a solution of 26.5 g of ammonium heptamolybdate in 100 ml of water, where a pH between 7 and 8 is established by addition of ammonia solution. The mixture is evaporated and the dried catalyst precursor is calcined at 600° C. for 12 hours. After cooling to room temperature, the catalyst is homogenized in a mortar and the powder is processed to a screening fraction (18 to 25 mesh).

The oxidation is carried out as described in Example 5. The results are given in Table 1.

Comparison Example 2

4 g of oxovanadium(IV)diphosphate are prepared according to the specifications as in DD Patent 113 210 and charged as a screening fraction into the reactor. In accordance with DD 298 234, Example 1, the starting material gas comprising 1.5% by volume of 4-chlorotoluene, 54% by volume of air and 44.5% by volume of steam (molar ratio 4-chlorotoluene:oxygen:water=1:7:30) is passed through the reactor at a residence time of 1.0 s. The reaction temperature is 425° C. To analyze the product stream, the process described in Example 1 is followed. At a conversion rate of 26%, the 4-chlorobenzaldehyde selectivity is 27%. The yield is 7%.

in which $Me^1$ is bismuth or vanadium, $Me^2$ is at least one of the elements selected from the group consisting of lithium, sodium, potassium, rubidium and cesium, $Me^3$ is at least one element selected from the group consisting of iron, cobalt, nickel, niobium, molybdenum, arsenic, tin, antimony, tungsten, tantalum, phosphorus, chromium, manganese, palladium, copper, zinc, cerium, silver, boron, samariuan, barium, calcium, magnesium and rhenium, and the letters a, b and c represent an atomic ratio of the respective elements such that when a=1, b has a value in the range from 0.1 to 2 and c has a value in the range from 0.05 to 2, different values for b and c being possible for different elements $Me^2$ or $Me^3$.

2. The process as claimed in claim 1, wherein $Me^3$ is at least one element selected from the group consisting of iron, cobalt, nickel, niobium, molybdenum, arsenic, tin, antimony and rhenium.

3. The process as claimed in claim 1, wherein $Me^1$ is vanadium, $Me^2$ is cesium and $Me^3$ is at least one element selected from the group consisting of iron, niobium, arsenic, tin, antimony, rhenium and tungsten.

4. The process as claimed in claim 1, wherein $Me^1$ is bismuth, $Me^2$ is cesium and $Me^3$ is at least one element

TABLE 1

| | Catalyst composition | Halotoluene | Reaction temperature (°C.) | Conversion rate Halotoluene (%) | Selectivity for the halobenzaldehyde (%) |
|---|---|---|---|---|---|
| Example 1 | $V_{1.0}Cs_{0.5}Fe_{1.0}O_x$ | 4-Chlorotoluene | 500 | 25 | 66 |
| Example 2 | $V_{1.0}Cs_{0.5}Fe_{1.0}Nb_{0.1}O_x$ | 4-Chlorotoluene | 400 | 13 | 86 |
| | | | 450 | 34 | 66 |
| Example 3 | $V_{1.0}Cs_{0.5}Fe_{1.0}Sn_{0.1}O_x$ | 4-Chlorotoluene | 500 | 68 | 33 |
| Example 4 | $V_{1.0}Cs_{0.5}K_{0.2}Re_{0.2}O_x$ | 4-Chlorotoluene | 500 | 5 | 98 |
| Example 5 | $V_{1.0}Cs_{0.5}Fe_{1.0}W_{0.1}O_x$ | 4-Chlorotoluene | 450 | 38 | 60 |
| Example 6 | $Bi_{1.0}Mo_{1.0}Cs_{0.5}Sb_{0.7}Sn_{0.7}Fe_{0.1}Co_{0.1}O_x$ | 4-Chlorotoluene | 450 | 24 | 77 |
| Example 7 | $Bi_{1.0}Mo_{1.0}Cs_{0.8}Sb_{1.7}Sn_{1.3}Fe_{0.1}Co_{0.1}O_x$ | 4-Chlorotoluene | 500 | 11 | 86 |
| Example 8 | $V_{1.0}Cs_{0.5}Fe_{1.0}Nb_{0.1}O_x$ | 2-Chlorotoluene | 450 | 32 | 64 |
| Example 9 | $Bi_{1.0}Mo_{1.0}Cs_{0.5}Sb_{0.7}Sn_{0.7}Fe_{0.1}Co_{0.1}O_x$ | 2-Chlorotoluene | 450 | 22 | 78 |
| Example 10 | $V_{1.0}Cs_{0.5}Fe_{1.0}W_{0.1}O_x$ | 4-Fluorotoluene | 450 | 17 | 73 |
| Comparison Example 1 | $Bi_{1.0}Mo_{1.0}O_x$ | 4-Chlorotoluene | 450 | 6 | 39 |

We claim:

1. A process for the preparation of halobenzaldehydes of the formula (I):

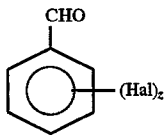
(I)

in which Hal is fluorine, chlorine, bromine or iodine and z=1, 2, 3 or 4, by catalytic gas-phase oxidation of a substituted toluene of the formula (II),

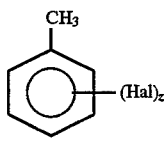
(II)

by oxygen, which comprises carrying out the oxidation in the presence of a catalyst of the formula (III)

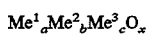

$Me^1_a Me^2_b Me^3_c O_x$ (III), selected from the group consisting of molybdenum, tin, antimony, iron and cobalt.

5. The process as claimed in claim 1, wherein the catalyst is present in pure form, is mixed with a support material or is fixed on a molded support material.

6. The process as claimed in claim 2, wherein the catalyst is used fixed on a support material.

7. The process as claimed in claim 1, wherein the support material used is alumina, ceramic, kieselguhr, silica gel, silicon carbide, fused silica or titanium dioxide.

8. The process as claimed in claim 3, wherein the catalyst is used in pure form.

9. The process as claimed in claim 1, wherein the oxidation is carried out in a fluidized bed or a fixed-bed reactor.

10. The process as claimed in claim 1, wherein the oxidizing agent used is a mixture of oxygen with an inert gas.

11. The process as claimed in claim 1, wherein the reaction temperature is 400° to 500° C.

12. The process as claimed in claim 1, wherein Hal is fluorine, chlorine or bromine in formulae (I) and (II).

13. The process as claimed in claim 1, wherein z is 1 or 2 in formulae (I) and (II).

14. The process as claimed in claim 1, wherein 2-chlorotoluene, 4-chlorotoluene, 4-fluorotoluene or 2-bromotoluene is used.

15. The process as claimed in claim 1, wherein the catalyst comprises $V_1Cs_{0.5-1}Fe_{0.5-2}(Nb, Sb, Sn, Re$ or $W)_{0.05-0.2}O_x$.

16. The process as claimed in claim 1, wherein the catalyst comprises $Bi_1Cs_{0.5-2}(Sb, Sn$ or a mixture thereof$)_{0.2-1.5}O_x$.

17. The process as claimed in claim 10, wherein the inert gas is nitrogen, carbon dioxide, argon, air or a mixture of noble gases.

18. The process as claimed in claim 17, wherein the inert gas is air.

19. The process as claimed in claim 12, wherein Hal is chlorine or bromine in formulae (I) and (II).

20. The process as claimed in claim 12, wherein Hal is chlorine in formulae (I) and (II).

21. The process as claimed in claim 13, wherein z is 1 in formulae (I) and (II).

* * * * *